United States Patent [19]

Green et al.

[11] 3,955,186

[45] May 4, 1976

[54] SAFETY SYSTEMS FOR MINIMIZING FIRE AND EXPLOSION HAZARD IN THE PRESENCE OF COMBUSTIBLE GASES

[75] Inventors: John Llewellyn Green, Old Harlow; Alan Frank Notschild, Harlow, both of England

[73] Assignee: Greenpar Heat Treatments Limited, Harlow, England

[22] Filed: Oct. 7, 1974

[21] Appl. No.: 512,961

[30] Foreign Application Priority Data

Jan. 23, 1974 Great Britain...........................3183

[52] U.S. Cl. ........................... 340/237 R; 137/78
[51] Int. Cl.² ....................................G08B 17/10
[58] Field of Search .........340/237 R; 324/71 SN; 73/23, 27 R; 137/312, 78

[56] References Cited

UNITED STATES PATENTS

| 3,609,732 | 9/1971 | Kobe et al. | 340/237 R |
| 2,219,391 | 10/1940 | Jacobson | 340/238 |
| 3,860,919 | 1/1975 | Aker | 340/237 S |
| 3,864,628 | 2/1975 | Klass et al. | 324/71 SN |
| 3,728,615 | 4/1973 | Hill et al. | 340/237 RX |

*Primary Examiner*—John W. Caldwell
*Assistant Examiner*—Daniel Myer
*Attorney, Agent, or Firm*—Larson, Taylor & Hinds

[57] ABSTRACT

A safety system for the detection of low concentrations of combustible gases which operates to turn off a fuel supply on detection of a combustible gas in which a transducer is employed, the heating element of the transducer being energized with short duration pulses generated by an astable multivibrator whilst the sensing element is connected in a circuit for detecting a flow of current between the heating element and the sensing element. On detecting the presence of gas, the fuel supply is switched off and thus rendered safe against a possible explosion or fire resulting if the gas escape went undetected. Energizing the heating element with short duration pulses enables the safety system to operate for long periods of time without needing attention.

10 Claims, 4 Drawing Figures

SAFETY SYSTEMS FOR MINIMIZING FIRE AND EXPLOSION HAZARD IN THE PRESENCE OF COMBUSTIBLE GASES

The present invention relates to a safety system for the detection of low concentrations of combustible gases such as hydrogen, carbon monoxide, methane, propane, butane or alcohol vapour. Some of these gases are commonly used for heating and lighting aboard ships, pleasure craft, or in caravans, the combustible gas being supplied in pressurized containers intended for this purpose.

The risk of fire or explosion represents a common and serious hazard for the owner of a yacht or caravan. There are a number of gas detectors available that give visual or audible alarm. The disadvantages of most types of known systems is that they are not designed to turn the gas supply off when a leakage of gas is detected. Thus if the premises is left unattended, the alarm emitted by available gas detectors could pass unnoticed until the entire contents of the gas cylinder had emptied itself into the yacht or caravan. In the case of a yacht, gas leakage can be particularly dangerous, because the type of gas commonly supplied is heavier than air and accumulates in the bilges.

One known type of safety system for the detection of low concentration of combustible gases is disclosed in United States Pat. No. 3,609,732. In this known system, a gas responsive switching device for detecting gas concentrations in air which uses a heated semiconductor having two electrodes embedded therein, a resistor connected in series with the electrodes and across a voltage source, and a thyristor and relay coil connected in series across the voltage source. The gas responsive switching device thus operates a relay or other switching circuit for opening and closing appropriate contacts having a sufficient current capacity to control any desired apparatus.

This type of safety system disclosed in United States Pat. No. 3,609,732 is unsuitable for many applications such as for example in caravans and yachts. Moreover, it will consume relatively large quantities of power when left switched on, which will be costly to the owner.

It is therefore an object of the present invention to overcome the above disadvantage of heavy power consumption when the device is left switched on for long periods of time.

According to the present invention there is provided a safety system for the detection of low concentrations of combustible gases which operates to turn off a fuel supply on detection of a combustible gas including: remote controlled valve means in the main supply of the fuel for turning said fuel supply "on" and "off"; at least one transducer position for detection of a combustible gas, said transducer having first and second elements; means for energizing said first element with short duration pulses from a voltage source; means for detecting a current flow between said two elements on detection of a gas; and means operable from the detected current flow to switch off said valve.

The safety system may additionally operate visible and/or audible alarm devices on the detection of a combustible gas. Furthermore, in the event that the system is protecting a confined or enclosed area, ventilation fans may be provided which are operated to extract the combustible gas from said area on detection.

More than one transducer may be provided whereby a plurality of points on a fuel distribution system may be monitored for the presence of combustible gases.

The transducer employed is preferably a sintered n-type semiconductor employing tin dioxide as the active element.

The short duration pulses supplied to the first element of the transducer are preferably generated with the use of an astable multivibrator having a mark space ratio chosen to suit the available D.C. supply voltage and the power requirements of the transducer. In the case of 24 volt supplies the mark space ratio is approximately 50 : 1.

Such a system of supplying short duration pulses to the heater element of the transducer greatly reduces the power consumption without affecting the operation of the safety system.

The present invention will now be described in greater detail by way of example with reference to the accompanying informal drawings, in which.

Figure 1:
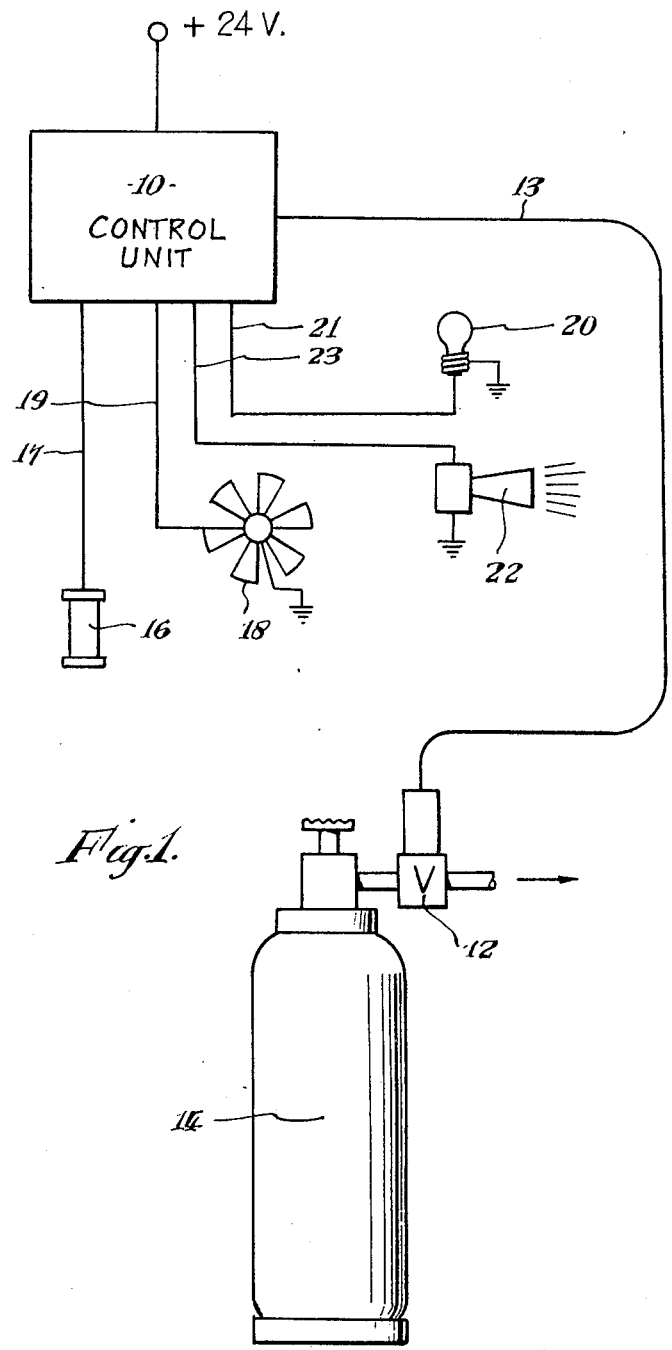
FIG. 1 shows one preferred form of safety system in schematic form for the detection of low concentrations of combustible gases.

Referring first to FIG. 1, the safety system includes a control unit 10 containing the power supply for the detector. The control unit 10 is connected to a 24 volt D.C. supply and is electrically connected to a remote gas valve 12 by means of an electrical lead 13, the gas valve 12 being fitted close to a gas cylinder 14. The gas valve 12 is normally "off" unless energized from the control unit 10. A gas detector 16 is connected to the control unit 10 by means of a conductor 17, the detector 16 being strategically located in a place where gas is likely to accumulate or be emitted. The safety system also includes a ventilation fan 18, a warning lamp 20 and a buzzer 22, which are respectively connected to control unit 10 by means of conductors 19, 21 and 23.

Figure 2:
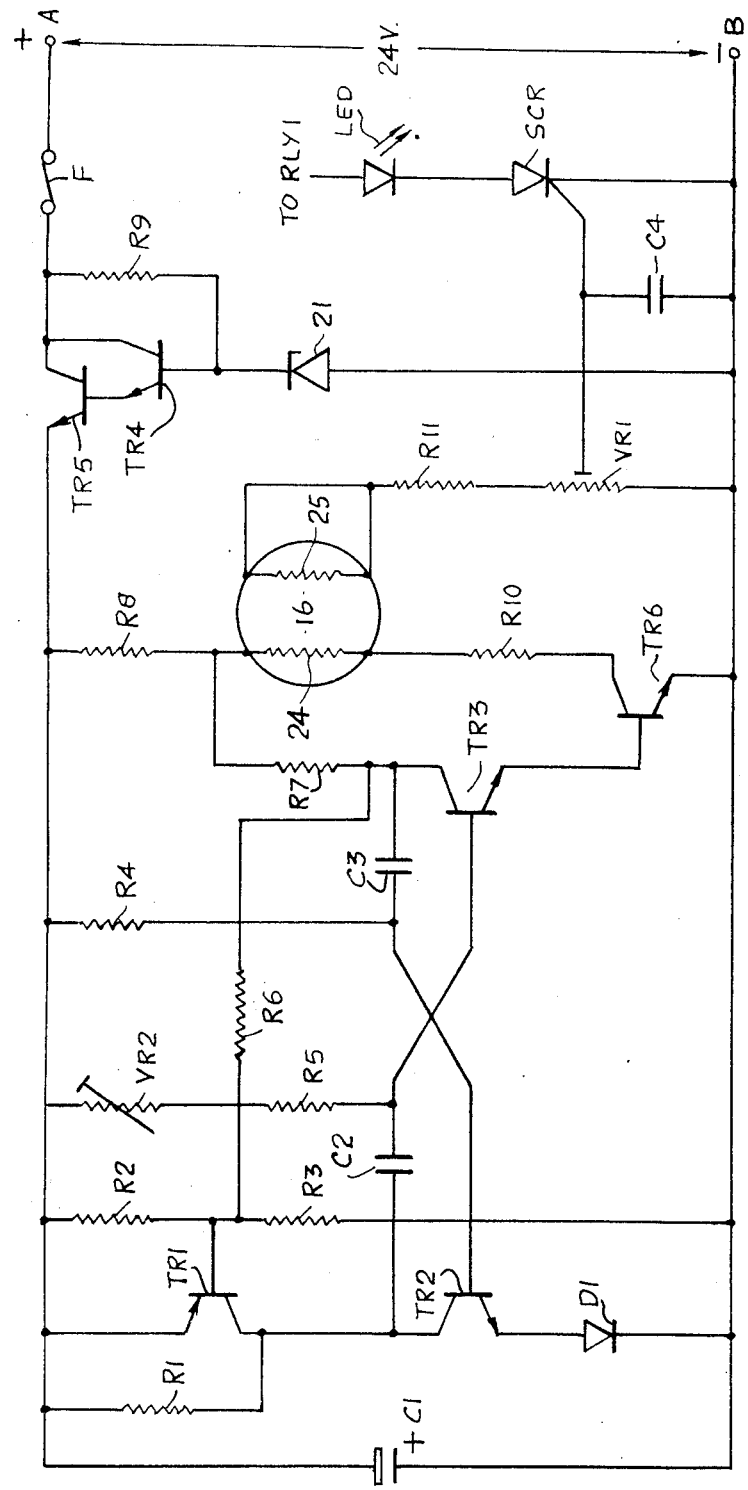
FIG. 2 shows the circuit diagram of the gas detector power supply.

FIG. 2 shows the circuit of the detector power supply intended for use with currently available sintered n-type semiconductor transducers employing tin dioxide as the active element whose electrical conductivity increases in the presence of combustible (reducing type) bases. The active element comprises a porous solid in which are located coils that serve as both heater and sensing electrode. The coils are made from a platinum/iridium alloy and have a resistance of approximately 2 ohms each. In air, the heated active element has a high resistance so that only a small current flows between the two electrodes. If a combustible gas is present a positive space charge occurs on the surface of the tin dioxide every time a gas molecule is captured. This increases the density of the conductor electrons in a space-charge layer just beneath the surface. Although, the tin dioxide is also minutely reduced to metallic tin causing the electrical resistance to decrease, it is the capturing process which in fact contributes more to the reduction in resistance rather than the creation of metallic tin. This process is reversible and any metallic tin formed will be converted to tin oxide by the atmospheric oxygen when the combustible gas is no longer present.

The increased conductivity of the device when exposed to even low concentrations of gas can be as high as 20 times that of its conductivity in air. Such a change can be brought about by the presence of 0.1% propane by volume which represents only 1/20 of the lower explosive limited for propane.

The detector requires a heater supply of 1.0 volt at 0.5 ampere (0.5 watt). In order to operate it from a 24 volt D.C. supply it would be logical to connect the heater in series with a voltage dropping resistor such that 23 volts are dropped in the resistor, the remaining 1 volt appearing across the heater. Such a circuit arrangement would be very wasteful of electrical energy as 11.5 watts would be dissipated in the voltage dropping resistor in the form of heat.

The detector 16 has two elements, firstly a heater element 24 and secondly a sensing element 25.

The control unit gas detector power supply includes transistors TR1 to TR6, resistors R1 to R11, capacitors C1 to C4, a diode D1, a zener diode Z1, a potentiometer VR1, a variable resistor VR2 and a thyristor SCR1 arranged to operate with the gas detector 16.

The components consisting of the transistors TR2 and TR3, the capacitors C2 and C3 and the resistors R4 and R5 together form an astable ultivibrator having a mark space ratio of 50 : 1. The supply to this astable multivibrator and also the detector 16 is obtained from the 24 volt D.C. supply which is regulated by means of a Darlington pair consisting of transistors TR4 and TR5. A fuse F is connected between the positive terminal A of the D.C. supply and the commoned collector electrodes of the Darlington pair TR4 and TR5. A resistor R9 is connected between the base electrode of the transistor TR4 and the commoned collector electrodes. A zenior diode Z1 is connected between the base electrode of the transistor TR4 and the negative terminal B of the power supply.

The first element 24 of the gas detector, which as stated above acts as the heater element is connected in series with resistors R8 and R10 and the transistor TR6. The resistor R8 is connected to the positive rail of the supply after it has been regulated and stabilized by means of the Darlington pair. The emitter electrode of the transistor TR6 is connected to the negative rail of the supply.

The collector electrode of the transistor TR2 is connected to the base electrode of the transistor TR3 through the capacitor C2. Likewise, the collector electrode of the transistor TR3 is connected to the base electrode of the transistor TR2 through the capacitor C3. The emitter electrode of the transistor TR2 is connected to the negative rail of the power supply through the diode D1. The emitter electrode of the transistor TR3 is connected to the base electrode of the transistor TR6.

The collector-emitter path of the transistor TR2 is connected in series with the collector-emitter path of the transistor TR1, across the positive and negative rails of the D.C. power supply. The base electrode of the transistor TR1 is connected to the junction between the resistors R2 and R3 which together form a potentiometer connected across the positive and negative rails of the power supply. This junction point is also connected to the collector electrode of the transistor TR3. The base electrode of the transistor TR2 is also connected to the positive rail of the D.C. power supply through the resistor R4, whilst the base electrode of the transistor TR3 is also connected to the positive rail through a series circuit consisting of the resistor R5 and variable resistor VR2. The collector electrode of the transistor TR3 is connected to the junction between the resistor R8 and the heater element 24 of the gas detector 16.

In operation, the astable multivibrator operates to switch the transistor TR6 off and on in the ratio of 50 : 1. Thus the supply to the heater element 24 of the gas detector 16 is in the form of short duration pulses, so that the gas detector is operated without wastage of electrical energy. This means that the gas detector can operate for long periods of time from a battery since the power dissipation is very low. Adjustment of the mark space ratio of the astable multivibrator can be achieved by altering the resistance in series with the resistor R5 with the aid of the variable resistor VR2. With a mark space ratio of 50 : 1 we have found that the average heat dissipation in the detector head is about 0.5 watt.

Because of the high mark space ratio required, the capacitor C2 is charged via a constant current source consisting of the transistor TR1 in order to achieve the required constancy of switching periods. The diode D1 prevents emitter-base breakdown of the transistor TR2 resulting from the high reverse voltage appearing at that point.

The second element 25 of the gas detector 16 has its two ends commoned together and connected to the negative rail of the supply through a resistor R11 and potentiometer VR1. The slider of the potentiometer VR1 is connected to the gate electrode of a thyristor SCR. The thyristor SCR is connected in series with the control unit 10 across the 24 volt D.C. power supply. A capacitor C4 is connected between the gate electrode and cathode of the thyristor SCR.

The electrical potential between the heater element 24 and the negative rail of the D.C. supply causes current to flow between heater element 24 and the sensing element 25 and through the potentiometer VR1. Depending upon the magnitude of the current between the two elements a varying voltage will appear across the potentiometer VR1. A voltage increase of sufficient magnitude appearing at the slider of the potentiometer VR1 triggers the thyristor SCR into conduction. Adjustment of the slider of the potentiometer VR1 enables the firing point of the thyristor SCR to be set to give the desired sensitivity, and the capacitor C4 decouples the gate electrode of the thyristor to eliminate any possibility of unwanted triggering due to spurious pulses.

When no gas is present, the resistance between the elements 24 and 25 is high, so that only a minimum current flows and the thyristor SCR is not triggered. When gas is detected, the resistance falls and a large current flows which triggers the SCR)

Figure 4:
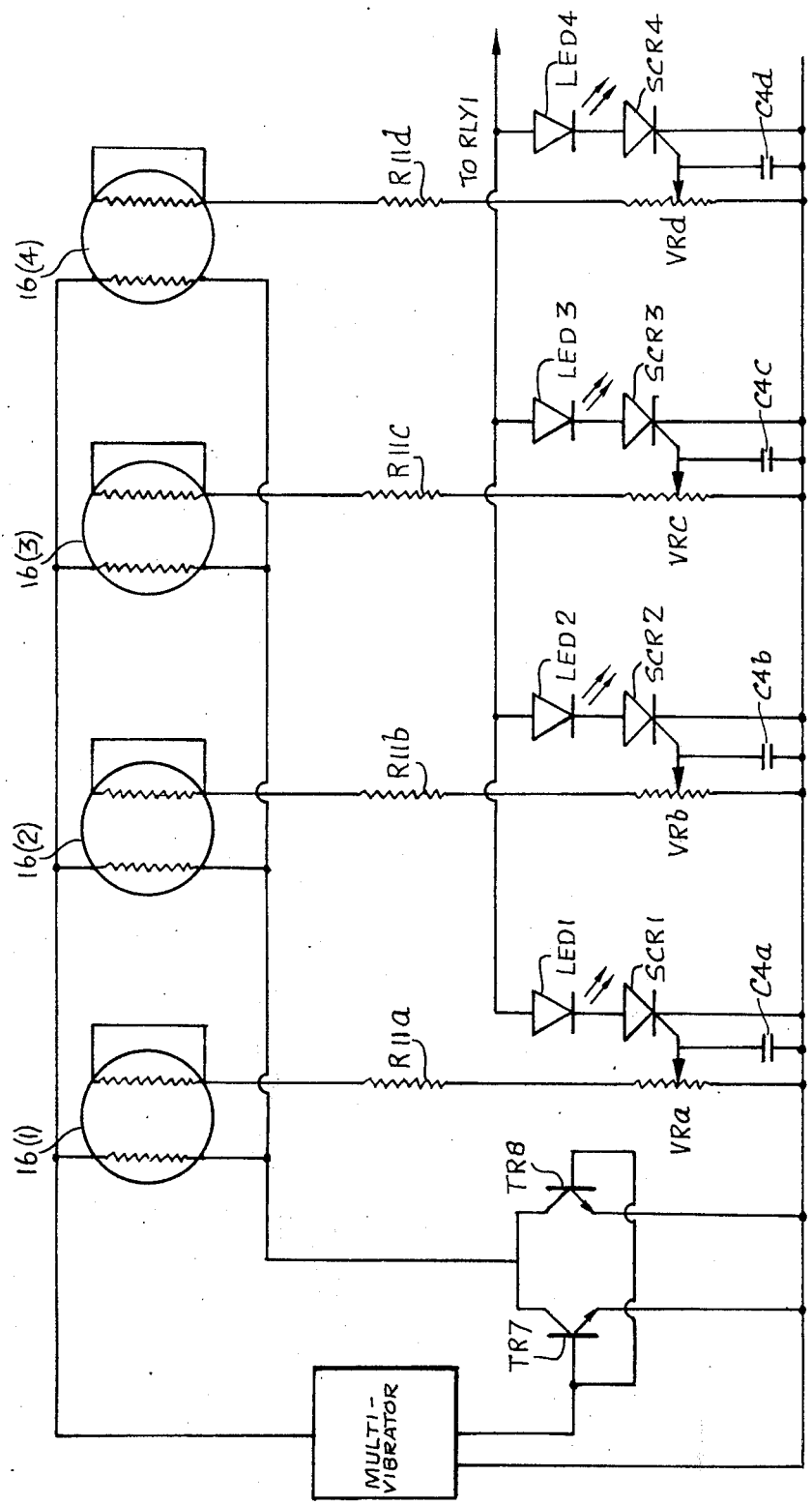
FIG. 4 shows a modified circuit of part of the gas detector power supply in the case where four detectors are connected in parallel.

Although in the circuit shown in FIGS. 1 and 2 only one gas detector is used, a second gas detector can be connected in parallel with the first. In this case a second SCR is provided so that the sensing element of the second gas detector can be connected to the gate electrode of the second SCR via a second potentiometer.

Where more than two gas detectors are used in parallel, the circuit requires further modification. FIG. 4 shows a prepared circuit arrangement where four gas detectors 16(1) to 16(4) are used, these gas detectors being placed at four strategic points where gas may leak or accumulate.

The astable multivibrator circuit is indicated by the block M, and the transistor TR6 is replaced by a pair of transistors TR7 and TR8 operating in parallel and connected in series with the parallel arrangement of all four heater elements of the gas detectors 16(1) to 16(4). Connected between the sensing elements of the gas detectors 16(1) to 16(4) and the hyristors SCR (1) to SCR (4) are respective resistors R11$a$ to R11$d$, potentiometers VR$a$ to VR$d$ and respective capacitors C4$a$ to C4$d$. Light emitting diodes LED1 to LED4 are connected in series with the respective thyristors SCR1 to SCR4.

Figure 3:
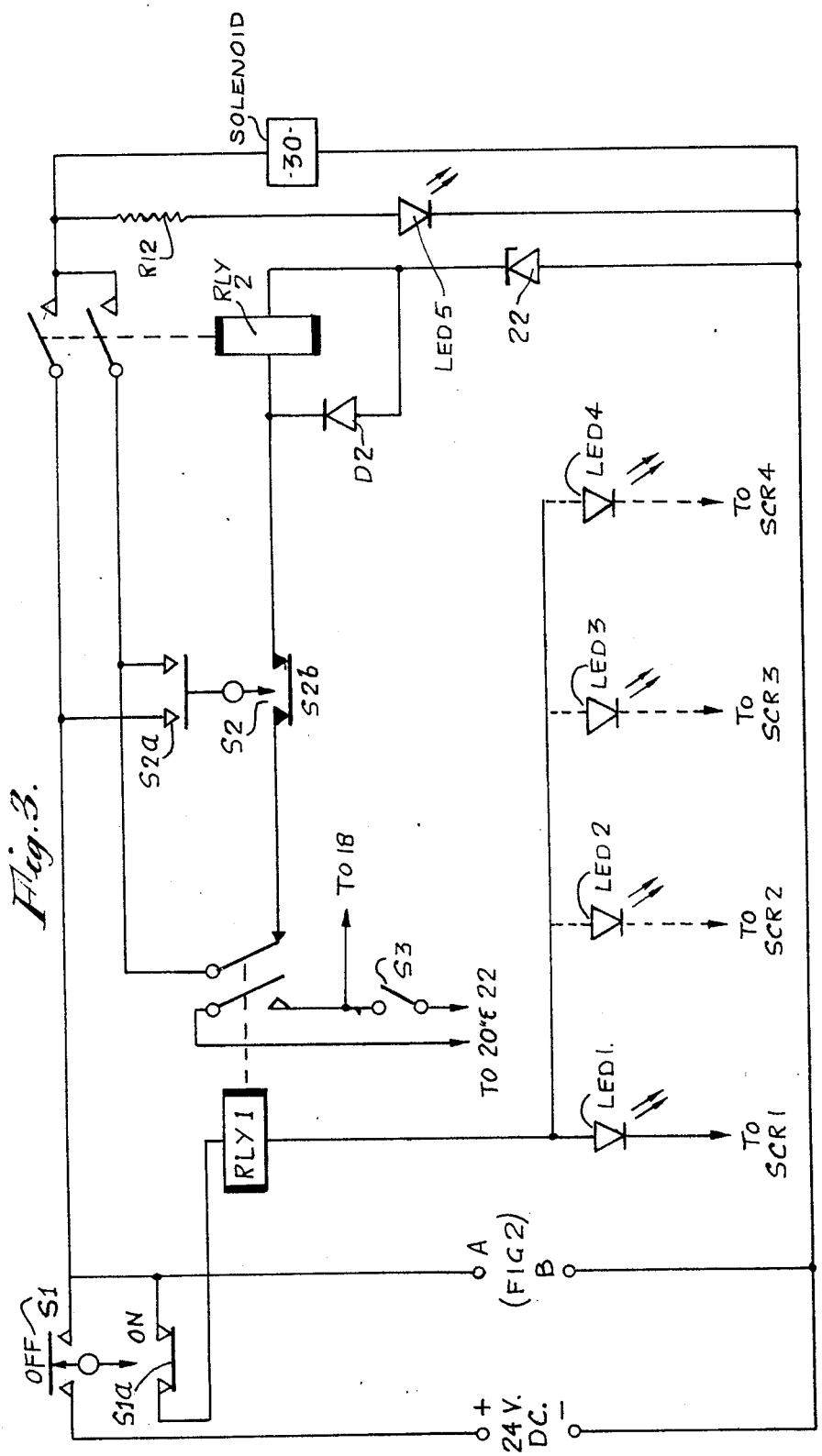
FIG. 3 shows the control switching and indicators connected to the detector power supply circuit.

The control switching and indicating circuit of FIG. 3 includes relays RLY1 and RLY2, each operating a pair of contacts; an ON/OFF switch S1 having reset contacts S1$a$; a centre biased toggle switch S2 having a "Gas on" contact S2$a$, and a "Gas off" contact S2$b$; an alarm ON/OFF switch S3; a "Gas on" solenoid 30; a resistor R12; a diode d2; a zener diode Z2; a "Gas on" indicator LED5 and "Gas Escape" indicators in the form of light emitting diodes LED1 to LED4 (if as many as four detectors are employed in the system as in the example shown in FIG. 4).

The switch S1 is a one-way biased toggle switch. This switch S1 is "off" in one position, "on" in the centre position, and provided with break contacts S1$a$ in the spring-biased position.

With the switch S1 in the "on" position the power supply circuit is energized via the positive and negative terminals A and B. When the centre-biased toggle switch S2$a$ is momentarily closed, the relay RLY2 is energized via the normally-closed contacts of the relay RLY1 and switch contacts S2. Relay RLY2 operates and closes both the latch contacts and the solenoid contacts; this operates the "Gas On" solenoid 30 and the "Gas On" indicator lamp LED5.

In the event of the thyristor SCR (FIG. 2) or one of the thyristors SCR1 to SCR4 being triggered into conduction by the presence of combustible gas, the "Gas Escape" indicator LED or the appropriate "Gas Escape" indicators LED1 to LED4 is illuminated and the relay RLY1 operates. This opens the contacts in the circuit supplying the relay RLY2, turning off the gas supply and extinguishing the "Gas On" indicator LED5. The switch S2$a$ becomes ineffective, thus preventing restoration of the gas supply, due to the relay RLY1 remaining in the energized state consequent upon the latching action of one of the thyristors SCR1 to SCR4. To reset the relay RLY1 to its non-energized state the supply is momentarily interrupted by the "reset" switch S1$a$. Should an inflammable gas still be present, the relay RLY1 will again operate and prevent restoration of the gas supply. A pair of contacts on the relay RLY1 are connected via the switch S3 to a terminal block in order that an external alarm may be connected. The switch S3 allows the alarm to be turned off if required.

The switch contacts S2$b$ permit the relay RLY2 to be unlatched, which allows manual remote control of the Gas ON/OFF function at any time, provided no fire hazard is present.

The diode D2 connected in parallel with the coil of the relay RLY2 quenches oscillatory voltage surges resulting from the inductance of the coil as it is switched on and off. The zener diode Z2 connected in series with the coil of the relay RLY2 prevents the relay from remaining latched should the supply voltage fall below 14 volts. This ensures that, with a failing battery supply, the gas will be turned off before the alarm circuit ceases to provide hazard protection.

In the above described system the combustible gas detectors are solid-state devices employing no diaphragms, switch contacts or other moving parts. They are thus unaffected by the vibration commonly encountered on board a ship.

In normal use the gas supply would be turned on and off by means of a switch on the control panel inside the yacht or caravan. The above described safety system thus affords a simple and absolutely foolproof way of isolating the gas distribution system from the pressurized gas container by cutting off the gas supply at source as soon as a combustible gas has been detected.

Moreover, the gas supply cannot be reinstated until the combustible gas has been removed from the area.

In the event of battery supply failure or the supply voltage falling below a given level, the gas supply is turned off but no alarm is indicated.

The safety system is adaptable to switch off the supply of liquid fuels as well as gaseous fuels. For example it could be used to switch off the supply of fuel to a diesel or petrol engine as soon as any form of combustible gas is detected in the vicinity of its fuel or the engine itself.

What we claim and desire to secure by Letters Patent is:

1. A safety system for the detection of low concentrations of combustible gases which operate to turn off a fuel supply on detection of a combustible gas including: remote controlled valve means in the main supply of the fuel for turning said fuel supply on and off; a solenoid for controlling said valve means; means for energizing said solenoid; a transducer positioned to detect the presence of a combustible gas, said transducer having first and second elements; an astable multivibrator having an off/on mark space ratio of approximately 50:1 for supplying low voltage short duration pulses to the first element of the transducer; a low voltage D.C. source for energizing both the solenoid and the astable multivibrator; a solid state element having a control electrode, said element being connected across the low voltage D.C. supply; a resistive circuit in series with the circuit across the elements of the transducer; means for connecting the control electrode of the solid state element to an appropriate point on the resistive circuit so that said solid state element will be caused to conduct when current flows in the resistive circuit due to the presence of gas; and relay means operable from the conduction of the solid state element for cutting off the supply to the solenoid and hence turning off the fuel supply.

2. A safety system according to claim 1, wherein the transducer is a sintered n-type semiconductor transducer employing tin oxide as the active element.

3. A safety system according to claim 1, additionally including a transistor, the emitter-collector path of said transistor being connected in series with the first element of the transducer, the base electrode of said transistor being connected to the output of the astable multivibrator, whereby the transistor operates as a switch to interrupt the current flow in the first element of the transducer so as to energize the transducer with said short duration pulses.

4. A safety system according to claim 1, additionally including an audible alarm device and a visible alarm device and contact means operable from said relay means for connecting said audible and visual alarms across the low voltage D.C. supply upon energization of said relay means due to the detection of combustible gas.

5. A safety system according to claim 4, additionally including ventilation means within the area being monitored for the detection of combustible gases, and contact means operable from said relay means for energizing the ventilation means upon energization of said relay means.

6. A safety system according to claim 1, wherein said solid state element is a silicon controlled rectifier and said resistive circuit includes a potentiometer connected between the two ends of the second element of the transducer and one side of the low voltage D.C. supply, the tap of the potentiometer being connected to the gate electrode of the silicon controlled rectifier.

7. A safety system for the detection of low concentrations of combustible gases which operates to turn off a fuel supply on detection of a combustible gas including: remote controlled valve means in the main supply of the fuel for turning said fuel supply on and off; a solenoid for controlling said valve means; means for energizing said solenoid; a plurality of transducers positioned at a plurality of different locations within an area to be protected, for detecting the presence of combustible gas within that area; first and second elements for each transducer; an astable multivibrator having an off/on mark space ratio such as to produce short duration pulses, the pulse being spaced apart by a length approximately equal to fifty times the width of each pulse; means for supplying the short duration pulses to the first elements of very transducer; a source of relatively low D.C. voltage for energizing both the solenoid and the astable multivibrator; as many solid state elements as there are transducers arranged in parallel across the D.C. supply; means for associating the control electrodes of the solid state elements with respective second elements of the transducers, such that said solid state elements will be rendered conductive when the current flows across the elements of the respective transducers; and relay means operable from the conduction of any solid state element for cutting of the energizing supply to the solenoid for closing said valve means.

8. A safety system according to claim 7, wherein said transducers are arranged in parallel and wherein said means for supplying the short duration pulses to the first elements of the transducers comprises a pair of transistors arranged with their collector-emitter paths in parallel and in series with the parallel arrangement of the first elements of the transducers.

9. A safety system according to claim 7, wherein each transducer has a potentiometer connected in series with its second element, the taps of the potentiometers being connected to respective gate electrodes of thyristors constituting the solid state elements, whereby current flows between the first and second elements of any transducer will cause the conduction of the associated thyristor.

10. A safety system according to claim 7, wherein each transducer is a sintered n-type transducer employing tin oxide as the active element.

* * * * *